United States Patent
Rich et al.

(10) Patent No.: US 8,013,013 B2
(45) Date of Patent: *Sep. 6, 2011

(54) FORMULATION AND DELIVERY METHOD TO ENHANCE ANTIOXIDANT POTENCY OF VITAMIN E

(75) Inventors: Melvin Lee Rich, Melville, NY (US); Ronald G. Udell, Beverly Hills, CA (US); Siva P. Hari, Riverside, CA (US)

(73) Assignee: Soft Gel Technologies, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/330,852

(22) Filed: Jan. 12, 2006

(65) Prior Publication Data

US 2006/0105034 A1    May 18, 2006

Related U.S. Application Data

(63) Continuation of application No. 10/720,957, filed on Nov. 24, 2003, now Pat. No. 7,015,245, which is a continuation of application No. 09/680,042, filed on Oct. 4, 2000, now Pat. No. 6,716,451.

(60) Provisional application No. 60/214,481, filed on Jun. 27, 2000, provisional application No. 60/168,199, filed on Nov. 30, 1999.

(51) Int. Cl.
*A61K 31/335* (2006.01)
*A61K 9/48* (2006.01)

(52) U.S. Cl. ....................................... 514/458; 424/451
(58) Field of Classification Search .................. 514/458; 424/451
See application file for complete search history.

(56) References Cited

U.S. PATENT DOCUMENTS

| | | |
|---|---|---|
| 2,940,900 A | 6/1960 | Benton, Jr. et al., |
| 3,102,078 A | 8/1963 | Robeson |
| 3,212,901 A | 10/1965 | Robeson |
| 3,564,097 A | 2/1971 | Magid |
| 4,364,945 A | 12/1982 | Whittle |
| 4,551,332 A | 11/1985 | Stillman |
| 4,612,194 A | 9/1986 | Ismail |
| 4,711,894 A | 12/1987 | Wenzel et al. |
| 5,102,659 A | 4/1992 | Hudson |
| 5,114,957 A | 5/1992 | Hendler et al. |
| 5,179,122 A | 1/1993 | Greene et al. |
| 5,348,974 A | 9/1994 | Wright et al. |
| 5,352,696 A | 10/1994 | Kim |
| 5,376,361 A | 12/1994 | Perricone |
| 5,387,579 A | 2/1995 | Meybeck et al. |
| 5,545,398 A | 8/1996 | Perricone |
| 5,591,772 A | 1/1997 | Lane et al. |
| 5,919,818 A | 7/1999 | Lane et al. |
| 5,948,769 A * | 9/1999 | Ismail ............................ 514/161 |
| 5,985,344 A | 11/1999 | Cherukuri et al. |
| 5,997,892 A | 12/1999 | Camp |
| 6,048,891 A | 4/2000 | Wechter |
| 6,239,171 B1 | 5/2001 | Lane et al. |
| 6,303,586 B1 | 10/2001 | McPeak et al. |
| 6,358,997 B1 | 3/2002 | Clark et al. |
| 6,716,451 B1 | 4/2004 | Udell et al. |
| 7,012,092 B2 | 3/2006 | Rich et al. |
| 7,015,245 B2 | 3/2006 | Rich et al. |
| 7,329,688 B2 | 2/2008 | Naguib et al. |
| 7,449,491 B2 | 11/2008 | Naguib et al. |
| 2001/0046548 A1 | 11/2001 | Berry et al. |
| 2004/0106674 A1 | 6/2004 | Rich et al. |
| 2004/0116512 A1 | 6/2004 | Naguib et al. |
| 2006/0106093 A1 | 5/2006 | Rich et al. |
| 2009/0156664 A1 | 6/2009 | Naguib et al. |

FOREIGN PATENT DOCUMENTS

| | | |
|---|---|---|
| JP | 7-163379 | 6/1995 |
| WO | WO 96/19218 | 6/1996 |
| WO | WO 2004/056348 | 7/2004 |

OTHER PUBLICATIONS

T.K. W. Ng. et al., "Effects of Tocotrienol-Rich and Tocopherol-Rich Fractions from Palm Oil 'on Serum Lipids and Platelet Aggregation in the Rat," 1990, Asean Food Journal, Asean Food Handling Bureau, Kuala Lumpur, MY, pp. 165-169, XP001038596, Issn: 0127-7324, p. 166, lines 11-15.

womensfitness.net, Comparison of Natural and Synthetic Vitamin E, Nov. 1, 2007, pp. 1-2.

Traber et al., http://Ipi.oregonstate.edu/ss02/blumberg.html, The Alpha-tocopherol Transfer Protein and Vitamin E Adequacy, May 2001, pp. 1-4.

Blumberg,http://Ipi.oregonstate.edu/ss02/blumberg.html, Unraveling the Conflicting studies on Vitamin E and heart disease, May 2002, 3 pages.

(Continued)

*Primary Examiner* — Brandon Fetterolf
*Assistant Examiner* — Shirley V Gembeh
(74) *Attorney, Agent, or Firm* — Dorsey & Whitney LLP

(57) ABSTRACT

A formulation to deliver a full-spectrum of Vitamin E isomers for improved antioxidant capacity, bioavailability, dissolution and efficacy. The formulation includes dl-α-tocopheryl acetate or dl-α-tocopheryl succinate (synthetic Vitamin E), natural Vitamin E and mixed tocopherols, such as α-, β-, γ- and δ-tocopherol, as well as four isomers (α, β, γ and δ) of tocotrienols. This formulation is designed to deliver at least 17-times the antioxidant capacity of synthetic Vitamin E (dl-α-tocopheryl acetate), and at least twice the antioxidant capacity of natural Vitamin E (d-α-tocopherol) as measured by oxygen radical absorbance capacity (ORAC) assay. The potent antioxidant capacity of this formula affords protection against oxidative damage of cell membranes, heart disease, cancer and eye and skin disease.

10 Claims, No Drawings

OTHER PUBLICATIONS

Burton et al., "Human Plasma and Tissue $\bar{\alpha}$-Tocopherol Concentration in Response to Supplementation with Deuterated Natural and Synthetic Vitamin E[1-5]", Am. J. Clin., Nutrition 67, pp. 669-684, 1998.
Fontenot, "Nutrition Forum: Can Vitamin E Prevent Heart Disease?", 1999, 3 pgs.
Amendment and Response to Office Action dated Dec. 4, 2009, U.S. Appl. No. 11/330,621, 10 pages.
Office Action dated Aug. 4, 2009, U.S. Appl. No. 11/330,621, 6 pages.
Brigelius-Flohe et al., "Vitamin E: function and metabolism," *The FASEB Journal*, Jul. 1999, vol. 13, pp. 1145-1155.
U.S. Appl. No. 11/330,621.
Office Action dated Mar. 12, 2010, U.S. Appl. No. 11/330,621, 13 pages.
U.S. Appl. No. 11/330,621.
Amendment and Response to Office Action dated Aug. 12, 2010, U.S. Appl. No. 11/330,621, 12 pages.
Kamat et al., "Tocotrienols from palm oil as effective inhibitors of protein oxidation and lipid peroxidation in rat liver microsomes," *Molecular and Cellular Biochemistry*, vol. 170, pp. 131-138, (1996).
womenfitness.net, "Comparison of Natural and Synthetic Vitamin E," Nov. 1, 2007, pp. 1-2.
U.S. Appl. No. 11/330,621.
Request for Continued Examination dated May 13, 2009, U.S. Appl. No. 11/330,621, 1 page.
Amendment Under Final dated May 13, 2009, U.S. Appl. No. 11/330,621, 9 pages.
Final Office Action dated Nov. 13, 2008, U.S. Appl. No. 11/330,621, 8 pages.
Amend and Response dated Aug. 14, 2008, U.S. Appl. No. 11/330,621, 11 pages.
Non-Final Office Action dated May 14, 2008, U.S. Appl. No. 11/330,621, 12 pages.
Amendment and Response dated Jan. 15, 2008, U.S. Appl. No. 11/330,621, 10 pages.
Non-Final Office Action dated Oct. 10, 2007, U.S. Appl. No. 11/330,621, 13 pages.
Request for Continued Examination dated Jun. 24, 2007, U.S. Appl. No. 11/330,621, 2 pages.
Advisory Action Before the Filing of an Appeal Brief dated Jul. 24, 2007, U.S. Appl. No. 11/330,621, 3 pages.
Amendment and Response dated May 24, 2007, U.S. Appl. No. 11/330,621, 10 pages.
Notice of Appeal to the Board of Patent Appeals and Interferences dated May 24, 2007, U.S. Appl. No. 11/330,621, 2 pages.
Final Office Action dated Nov. 24, 2006, U.S. Appl. No. 11/330,621, 9 pages.
Amendment and Response dated Sep. 11, 2006, U.S. Appl. No. 11/330,621, 14 pages.
Terminal Disclaimer (five) dated Sep. 11, 2006, U.S. Appl. No. 11/330,621, 10 pages.
Non-Final Office Action dated Mar. 10, 2006, U.S. Appl. No. 11/330,621, 11 pages.
U.S. Appl. No. 09/680,042.
Office Action dated Jul. 8, 2003, with Office Action of Dec. 18, 2001 attached, U.S. Appl. No. 09/680,042, 10 pages.
Amendment dated Jul. 25, 2003, U.S. Appl. No. 09/680,042, 10 pages.
Notice of Allowance and Fee(s) Due dated Nov. 4, 2003, 3 pages.
Amendment After Allowance dated Nov. 21, 2003, 9 pages.
Response to Rule 312 Communication dated Feb. 26, 2004, 3 pages.
U.S. Appl. No. 10/720,957.
Notice of Allowance and Fee(s) Due dated Oct. 21, 2006, U.S. Appl. No. 10/720,957, 7 pages.
Response dated Aug. 8, 2005, U.S. Appl. No. 10/720,957, 9 pages.
Terminal Disclaimer dated Aug. 8, 2005, U.S. Appl. No. 10/720,957, 2 pages.
Non-Final Office Action dated Apr. 8, 2005, U.S. Appl. No. 10/720,957, 5 pages.
Non-Final Office Action dated Oct. 26, 2004, U.S. Appl. No. 10/720,957, 5 pages.
Response dated Oct. 26, 2004, U.S. Appl. No. 10/720,957, 9 pages.
Non-Final Office Action dated Nov. 24, 2003, U.S. Appl. No. 10/720,957, 5 pages.
U.S. Appl. No. 10/720,907.
Notice of Allowance and Fee(s) Due dated Sep. 30, 2005, U.S. Appl. No. 10/720,907, 7 pages.
Non-Final Office Action dated Mar. 7, 2005, U.S. Appl. No. 10/720,907, 8 pages.
Amendment and Response dated Jun. 7, 2005, U.S. Appl. No. 10/720,907, 14 pages.
Response dated Oct. 20, 2004, U.S. Appl. No. 10/720,907, 9 pages.
Non-Final Office Action dated Oct. 16, 2004, U.S. Appl. No. 10/720,957, 4 pages.
Request for Continued Examination and Amendment and Response to Final Office Action dated Apr. 12, 2011, U.S. Appl. No. 11/330,621, 12 pages.

* cited by examiner

FORMULATION AND DELIVERY METHOD TO ENHANCE ANTIOXIDANT POTENCY OF VITAMIN E

FIELD OF THE INVENTION

This invention relates to a novel formulation and application of a blend of various isomers of Vitamin E, including synthetic Vitamin E, natural Vitamin E, mixed tocopherols, and tocotrienol isomers for synergistic and enhanced antioxidant capacity.

BACKGROUND OF THE INVENTION

Vitamin E is commonly found in vegetation and more abundantly in seeds from which tocopherols, in the natural state, are easily absorbed and utilized in humans and animals, wild and domestic. Nutritional supplements of natural or synthetic Vitamin E normally are administered by injection or orally. Tocopherols tend to be unstable molecules so to provide tocopherol with a reasonable shelf life, tocopherols are normally supplied with an acetate or succinate group, making Vitamin E acetate or succinate (d- or dl-α-tocopheryl acetate or succinate). These modifications decrease the bioavailability of tocopherol and therefore increase the cost of maintaining a desirable level of Vitamin E in the cells of a body, so that it can provide protection against cell component oxidation. In some species, both the α-tocopherol and α-tocopheryl acetate even in water dispersible forms are not bioavailable.

Enhanced absorption of Vitamin E acetate has been studied previously by using aqueous dispersions and solubilized preparations. It is well known that the efficacy of the hydrophilic nature of aqueous Vitamin E solutions and dispersions upon internal absorption of Vitamin E can be demonstrated by increased absorption of hydrophilic Vitamin E by the normal and compromised intestine. It is known in the art that the source of Vitamin E, natural or synthetic, also affects its bioavailability. The beneficial effects of tocotrienols include cholesterol lowering, antioxidant activity, tumor suppressive effect and inhibition of blood platelet aggregation.

The advantage of administering Vitamin E in a water-dispersible formulation was shown by Bateman et al. (J. Pharm. Pharmacol., 1984, 37(7), 461-464) in a human clinical study in which Vitamins A, E, and B.sub.2 were formulated into a liquid vehicle (Aqua Biosorb) and encapsulated into soft gelatin capsules, which were given orally.

Brooks describes in U.S. Pat. No. 3,253,992 the composition of anhydrous water dispersible fat soluble vitamin preparations and aqueous dispersions of these preparations.

Stillman in U.S. Pat. No. 4,551,332 teaches the use of frozen solutions of Vitamin E blends comprised of glyceryl mono- and distearate and in some cases Jojoba oil for dermatological and cosmetic applications.

Greene, et al. in U.S. Pat. No. 5,179,122 teaches a composition for an aqueous dispersible, free-flowing solid with enhanced bioabsorption and easy handling is a lipid melt blend comprised of a lipid soluble melt blended Vitamin E as the active ingredient and surface active agents to correct the hydrophilic/lipophilic balance (HLB). Vitamin E blend and surface active agents both comprise the melt blend which is absorbed onto an inert carrier to absorb the melt blend.

In fact, Vitamin E is a generic name for a family of four isomers of tocopherols and four isomers of tocotrienols. All 8 isomers have a 6-chromanol ring structure and a side chain. There are 4 tocopherols (α, γ, β, and δ) with a fully saturated side chain. The 4 tocotrienols (α, γ, β, and δ), although structurally similar to tocopherols, have unsaturated side chains with double bonds at the 3', 7', and 11' positions in the side chain. Individual tocopherols and tocotrienols differ from each other in the number and position of methyl groups in the aromatic chromanol ring. All isomers of Vitamin E exert a wide spectrum physiological effect. For example in addition to being antioxidants, tocotrienols have been shown to be potent suppressers of B16 melanoma cell proliferation in vitro, and γ-tocotrienol has been shown to inhibit the growth of human breast cancer cell growth in vitro more effectively than the popular breast cancer drug, Tamoxifen.

The Vitamin E isomers are light yellow oils at room temperature and are fairly stable to heat and acid, and degrade with alkaline conditions, when exposed to ultra violet light, and when exposed to the oxygen in air. However, recently, the term Vitamin E has become synonymous with only α-tocopherol and therefore, most retail Vitamin E supplements contain predominantly α-tocopherol.

Vitamins are grouped on the basis of solubility in water or oil (fat). As aforesaid, fat-soluble vitamins, like Vitamin E, are found in foods associated with lipids and are absorbed from the intestine with dietary fats. Therefore, Vitamin E intake is recommended with a meal, and normally 20 to 40% of the ingested Vitamin E prepared and delivered in accordance with the prior art, is absorbed. Foods that are rich in Vitamin E include dark green vegetables, eggs, fish, nuts, organ meats, soy beans, vegetable oils, wheat germ, and whole-grain products. However, foods are commonly depleted of Vitamin E due to processing, refining and storage. After absorption in the intestine, Vitamin E is transported to the blood circulation by lipoproteins. As a fat-soluble vitamin, Vitamin E is amenable for entry and storage in cell membranes.

The hallmark of Vitamin E isomers is their sacrificial antioxidant property due to the ease with which oxidation occurs in Vitamin E isomers with respect to other molecules in the body. Vitamin E is the primary defense against cell membrane and DNA damage and protects LDL and other lipid-rich biochemicals against oxidation. Thus, Vitamin E prevents the oxidation of unsaturated and polyunsaturated fatty acids. The need for Vitamin E is directly related to the polyunsaturated fatty acids or fish oil content of the diet since these have elevated peroxidative potential.

Research studies, in the past decade indicate that major diseases that afflict humankind worldwide may be preventable by the intake of nutrient substances, namely antioxidants. The term "antioxidant" nutritional agent has been applied to a number of specific nutrients, especially to Vitamin E. Antioxidant use therefore has gained popularity to prevent disease and to promote health. These compounds are readily available, nontoxic, and the usual intake varies in individuals depending on the diet.

To appreciate antioxidants, one must understand "free-radicals", which are unstable, highly reactive oxygen molecules (ions) that circulate in the bloodstream. To become chemically stable, free-radicals snatch electrons from other molecules in the body, a process that causes cell damage (oxidative damage). Antioxidants prevent oxidative damage by donating electrons to free-radicals. As a fat-soluble vitamin, Vitamin E is amenable for entry and storage in cell membranes to absorb free-radical molecules and reduce the damage they cause.

The normal metabolic processes release some free-radicals, but our body repairs most of the oxidative damage these natural free radicals cause. However, if we flood our bloodstream with an unusually large number of free radicals, typically by smoking or by eating a high-fat diet, over time, oxidative damage can overwhelm the body's repair mechanisms, setting us up for degenerative diseases. Antioxidants protect cells from the damage caused by free-radicals, unstable compounds that result from lifestyle factors like environmental stress and strenuous exercise, as well as natural processes like aging.

Tocotrienols, due to their unsaturated side chains, provide much stronger antioxidant effect and protect-against oxidation of "bad" cholesterol, LDL, which, if oxidized, leads to buildup of plaques in arteries and increased risk of heart attack or stroke.

α-tocotrienols have demonstrated superior antioxidant potential against iron induced lipid peroxidation in animal studies. Furthermore, tocotrienols caused regression in carotid artery stenosis or narrowing while acting as potent antioxidants in preventing coronary heart disease.

Various forms of the α-tocopherols have varying activity. Until now, most active isomer was d-α-tocopherol. Vitamin E supplements are stabilized and supplied as either the acetate or succinate esters.

Insufficient Vitamin E results in free-radical mediated lipid peroxidation of membranes and their destruction. Vitamin E protects the skeletal muscles, nervous system, and retina of the eye from oxidation. Vitamin E is essential for normal immune function. Vitamin E mitigates the prostaglandin driven severity of inflammation, PMS and circulatory disorders (leg cramps at night and sticky blood platelets). Vitamin E may reduce the toxicity of metals and protect against free-radical promoting environmental pollutants such as ozone, oxides of nitrogen (NOx), drugs, alcohol and smoking. Vitamin E inhibits the conversion of nitrites in smoked, barbecue, pickled and cured foods to carcinogenic nitrosamines in the body. Nearly 60% of the factors that affect health depend on lifestyle and exposure to risk factors. Aging is essentially oxidative deterioration of tissues. Since Vitamin E can prevent or slow down reactions of such oxidative damage, Vitamin E may slow the aging process. The importance of antioxidants stems from the number and breadth of diseases where they play a preventive role, such as heart disease, cancer, and eye disease. Furthermore, lack of significant toxicity in its use and the ease of use as a nutritional supplement attest to the significance Vitamin E.

Epidemiological studies suggest that low blood levels of Vitamin E are associated with increased risk of development of degenerative diseases including coronary heart disease, Alzheimer's disease, cataracts, and certain types of cancer. Two epidemiological studies of more than 12,000 adults conducted at Harvard University found a 40% decrease in heart disease risk in subjects taking at least 100 IU of Vitamin E daily. However, people taking a higher dose of Vitamin E supplements with only α-tocopherol may not be realizing full benefit. This is further substantiated by a recent study indicating that γ-tocopherol traps mutagenic electrophiles such as NOx and complements α-tocopherol.

Oral doses of Vitamin E ranging from 50 to 400 International Units (IU) per day did not show any adverse effects in double-blind clinical studies. The recommended daily amount (RDA) is 8 to 10 mg per day for healthy adults. In the U.S., 400 IU soft gelatin capsules are the most popular dosage form of Vitamin E. To achieve the potency of a 400 IU capsule, a person needs to consume 454 g of sunflower seeds, 2.2 Kg of wheat germ or 1.9 liters of corn oil totaling 8,000 calories daily. In 1993, 33% of Vitamin E supplement users took 400 IU/day. 51% took the Vitamin E in capsule form and 26% took the tablet form of Vitamin E. The RDA of tocotrienols ranges from 25 to 60 mg.

α-tocopherol is fairly stable to heat, but loses potency on exposure to air, heat and light. Similarly, tocotrienols are heat stable. If Vitamin E supplements are enclosed in a soft gelatin capsule and stored in a cool, dark place, they retain potency for at least 3 years. The esters of α-tocopherol are considerably more stable in soft gelatin capsules. However, Vitamin E supplements when spray dried and stabilized by excipients also retain potency. Recent research indicates that α-tocopherol and its acetate ester are equally effective in humans.

Fat-soluble vitamins, like Vitamin E, are found in foods associated with lipids and are absorbed from the intestine with dietary fats. Therefore, Vitamin E intake is recommended with a meal and normally 20 to 40% of the ingested Vitamin E is absorbed. Multiple doses instead of a single dose of Vitamin E taken daily with a meal seem to indicate increased absorption and utility in the body. In fact, a combination of tocopherols, tocotrienols and phospholipid emulsifier have been shown to be effective carrier of molecules for improved absorption. In cardiovascular clinical studies, 50 mg/day Vitamin E was used for a periods ranging from 1 to 8.2 years without any adverse effects. Vitamin E is the least toxic among the fat-soluble vitamins. No evidence of detrimental effects of Vitamin E is observed even at daily doses of 100 to 500 mg. Human studies at daily 240 mg doses of tocotrienols for 18-24 months did not indicate any adverse effects. Further animal studies show safety of tocotrienols up to 12,000 mg/day.

Reactive oxygen species are of great interest in medicine because of overwhelming evidence relating them to aging and various disease processes such as atherosclerosis, brain dysfunction, birth defects, cataracts, cancer, immune system decline, rheumatoid arthritis, and inflammatory bowel diseases. A complex antioxidant network is effective to counteract reactive oxygen species that are detrimental to human life, such as Vitamin E.

Only recently have reliable analytical methods become available to quantitatively measure the total antioxidant capacities, such as oxygen radical absorbance capacity (ORAC) assay, to evaluate the potency of antioxidant formulations. The ORAC method utilizes a peroxyl radical generator and beta-phycoerythrin protein as an indicator of oxidation by measuring the fluorescence of the protein. The ORAC values are expressed as micromoles of Trolox (6-hydroxy-2, 5,7,8,-tetramethylchroman-2-carboxylic acid) equivalents per liter of the sample and Trolox shows total inhibition of the peroxyl radical action.

The ORAC assay is a widely accepted method in the world for identifying the antioxidant potential in a sample/product. The samples can be a pure compound, blood plasma, various tissues and foods such as fruits, vegetables, or dietary supplements. The total antioxidant capacity is reflected from various antioxidants present in the sample and their interactions. For example, the ORAC values of antioxidant dietary supplements varies from 10 to 4,000 micromoles per gram. The advantage of this assay is that it helps quantify the antioxidant potential value of a sample compared to other commercial samples/sources.

Several other methods have been developed to measure the total antioxidant capacity of a sample. However, the peroxyl or hydroxyl radicals used in the ORAC assay as pro-oxidants make it different and unique from the other assays that involve oxidants that are not necessarily pro-oxidants. Further, substantial deficiencies of other methods have been overcome in the ORAC assay. For example, the ORAC assay was compared to other assays and the ORAC assay seems to provide a better correlation to the antioxidant capacity. Therefore, the ORAC assay method provides a valuable tool with which a researcher can quickly determine the value of a particular formulation, where increased potency and reduced cost are desired. The present full spectrum Vitamin E formulation delivers at least 17 times the antioxidant capacity of synthetic Vitamin E and twice the antioxidant capacity of natural Vitamin E.

Recent research has increased the popularity of the therapeutic and prophylactic advantages of Vitamin E and its antioxidant effects. Soft gel encapsulation of Vitamin E is safe and protects the potency of the ingredients and ensures a consistent level of active ingredients. Soft gels are easy to swallow and mask any unpleasant taste or odor associated with some of the ingredients. Soft gel capsules dissolve quickly and provide for rapid absorption of the active ingredients and soft gels do not need the fillers and binders used in most tablets and powders, although pigments are sometimes used for cosmetic value.

Vitamin E can be provided in other forms, such as tablets and powders, where the active ingredients (which are oils) are placed on the surface of a carrier such as starch or maltodextrin. However, the present invention can be provided in any of the common dosage or delivery forms.

SUMMARY OF THE INVENTION

The present invention comprises stable and nontoxic formulations of natural and synthetic Vitamin E, mixed tocopherols, and tocotrienols. Such formulations improve the antioxidant capacity of a given dosage over and above that of natural and synthetic Vitamin E formulations as measured by ORAC assays. A preferred soft gel formulation includes synthetic Vitamin E, natural Vitamin E, mixed tocopherols, tocotrienols and soybean oil as an economical non-interacting carrier for administration once a day. Tocotrienols are related to Vitamin E. Palm and rice are rich and natural sources of the tocotrienols used in the formulation, but cost effective synthetic tocotrienols may be available in the future. Tocotrienols by themselves can not replace Vitamin E, but with their individual potency and distinct protective roles, they complement Vitamin E. Hence, the potent blend of Vitamin E, tocopherols and tocotrienols in the present formulation provide optimal synergy.

It is therefore an object of the present invention to provide improved formulations of a full complement of Vitamin E isomers including tocotrienols, which produce a significantly synergistic antioxidant capacity of the formulations that is greater than in heretofore known formulations or delivery systems.

It is another object of the present invention to provide Vitamin E formulations, which have surprisingly large antioxidant capacities, and can be provided in any dosage or delivery forms compatible with ordinary Vitamin E formulations, such as soft gel, tablet, powder, suppository, micellar, and injectable forms, or any other delivery systems and can provide such beneficial antioxidant to living beings, whether human or other animals.

It is another object of the present invention to provide a reduced cost soft gel formulations of full spectrum Vitamin E, with an enhanced antioxidant capacity as shown by ORAC assays.

DETAILED DESCRIPTION OF THE PREFERRED EMBODIMENTS

The unique formulation of the present invention involves the following sequence of ingredients and quantitative analysis by ORAC assay.

The formulation is made by simultaneous addition under vacuum of: dl-α-tocopheryl acetate or dl-α-tocopheryl succinate (which are interchangeable), natural Vitamin E, mixed tocopherols, and tocotrienols. A solvent, such as soybean oil, is added as required to achieve the proper flow characteristics. All the ingredients are blended and continuously stirred for about one hour. After thorough mixing, the container of the mixture is blanketed with nitrogen gas to prevent oxidation. The above mixture normally is then encapsulated as a soft gel or spray dried onto the surface of a filler or carrier for powder or tablet form. However the mixture is compatible with other dosage or delivery forms.

The resultant ingestable dosage for humans preferably contains 5 to 2000 mg d-α-tocopherol (natural Vitamin E), 5 to 2000 mg of dl-α-tocopheryl acetate or succinate (synthetic Vitamin E), 5 to 2000 mg of natural mixed tocopherols including α, γ, β, and δ isomers, 5 to 500 mg of tocotrienols including α, γ, β, and δ isomers, and vegetable oil such as rice bran or soybean oil. Currently, the preferred source for tocotrienols is either rice or palm, but economical synthetic tocotrienols may be available in the future, and are suitable for the formulations. For large animals, the amount of ingredients in a single dosage may be increased by up to an order of magnitude or multiple dosages may be provided. The components in these formulations form a comprehensive antioxidant formula to assist the cell membrane lipid bilayer from free radical peroxidation and result in an antioxidant capacity that is at least twice as large as an equivalent Vitamin E amount of any one of the components.

Economics as well as the synergistic beneficial effects of the ingredients are the major driving forces as to the relative percentages of natural and synthetic Vitamin E included in the formulation. Therefore, as economics vary, the synergistic effects of the ingredients in the formulations are maintained while varying the formulations for lowest cost. At the present time, natural Vitamin E with mixed tocopherols and natural Vitamin E (d-α-tocopherol) is about twice as expensive as synthetic Vitamin E and tocotrienols are about 20 times more expensive than synthetic Vitamin E. Therefore, for any target potency (anti-oxidant capacity), generally maximum synthetic Vitamin E and minimum tocotrienols are desired. The ranges above represent possible formulations assuming the costs of the various active ingredients vary considerably. Supply or manufacturing problems may make tocotrienols from palm or synthetically constructed, preferred in the future.

Since they normally are extracted form natural sources, the preferred product composition of each isomer of tocopherol and tocotrienol may vary depending on the source and blend of the constituent raw materials. Normally, a 5% overage is incorporated beyond that of the label claims since natural ingredients are notoriously fickle in the amount of active substance actually present from batch to batch.

As discussed above, the present invention is a unique blend since it provides an alternative to either natural Vitamin E products or synthetic Vitamin E or tocotrienol products. The efficacy and synergy of the synthetic Vitamin E is enhanced by the addition of natural Vitamin E, mixed tocopherols and tocotrineols. The formulation is a unique blend with measurable antioxidant capacity to help promote antioxidant protection particularly for the human body, at less cost per actual antioxidant capacity delivered than heretofore available formulations which come in a once a day, swallowable form.

At the present time, the following formulations for a 400 IU size 11 oblong soft gel capsule are preferred considering short term historical cost variations. The formulations all have essentially the same potency as measured by the ORAC assay, about twice that of the most potent natural Vitamin E.

| Ingredient | Fill Active | Label Amount |
|---|---|---|
| Formulation I | | |
| dl-α-tocopheryl acetate | 320.0 mg | 320.0 IU |
| 70% mixed tocopherols | 60.0 mg | 320.0 IU |
| α-tocopherol | (9.6%)/(5.7 mg) | 8.5 IU |
| β-tocopherol | (1.0%) | 600.0 mcg |
| γ-tocopherol | (42.0%) | 24.0 mg |
| δ-tocopherol | (13.0%) | 7.8 mg |
| Oryza Oil, 16% tocotrienols | 33.0 mg | 5.3 mg |
| α-tocotrienol | (8.0%) | 2.6 mg |
| β-tocotrienol | (0.1%) | 33.0 mcg |
| γ-tocotrienol | (42.0%) | 2.6 mg |
| δ-tocotrienol | (13.0%) | 99.0 mcg |
| α-tocopherol | (13.0%)/(4.3 mg) | 6.3 IU |
| β-tocopherol | (0.3%) | 99.0 mcg |
| γ-tocopherol | (1.2%) | 390.0 mcg |
| δ-tocopherol | (0.2%) | 66.0 mcg |
| d-α-tocopherol | 80.0 mg | 80.0 IU |
| soybean oil | 57.0 mg | inactive |
| Formulation II | | |
| dl-α-tocopheryl acetate | 320.0 mg | 320.0 IU |
| 70% mixed tocopherols | 60.0 mg | 320.0 IU |
| α-tocopherol | (9.6%)/(5.7 mg) | 8.5 IU |
| β-tocopherol | (1.0%) | 600.0 mcg |
| γ-tocopherol | (42.0%) | 24.0 mg |
| δ-tocopherol | (13.0%) | 7.8 mg |
| Oryza Oil, 16% tocotrienols | 23.0 mg | 3.7 mg |
| tocotrienols (from Palm) | 10.0 mg | 1.6 mg |
| d-α-tocopherol | 80.0 mg | 80.0 IU |
| soybean oil | 57.0 mg | inactive |
| Formulation III | | |
| dl-α-tocopheryl acetate | 320.0 mg | 320.0 IU |
| 70% mixed tocopherols | 60.0 mg | 320.0 IU |
| α-tocopherol | (9.6%)/(5.7 mg) | 8.5 IU |
| β-tocopherol | (1.0%) | 600.0 mcg |
| γ-tocopherol | (42.0%) | 24.0 mg |
| δ-tocopherol | (13.0%) | 7.8 mg |
| tocotrienols (from Palm) | 33.0 mg | 5.3 mg |
| d-α-tocopherol | 80.0 mg | 80.0 IU |
| soybean oil | 57.0 mg | inactive |

The preferred formulation is normally processed into soft gel form using the Iso-Lock, UltraFill 80 technology to allow a suspension formula to be created with water-soluble Vitamin E and tocotrienol ingredients as well making this invention not just made of oil blends, but capable of being made as suspensions as well.

The blend may contain inseparable variable content of carotenoids including alpha carotene, beta carotene, gamma carotene, lycopene, and phytosterols and squalene. The blend may also include, but is not limited to, 1 to 50 mg of the following antioxidants as markers or as functional antioxidants so that the manufacturing site can be traced from the ingredients in case there is a need to determine the authenticity of a particular capsule: coenzyme Q10; rosemary oil; green tea; α lipoic acid; lycopene; grape seed extract; pine bark extract Vitamin C; natural beta carotene; synthetic beta carotene; γ-oryzanol (esters of ferrulic acid); selenium; and lutein.

To provide the formulation in tablet or powder form, any of the above formulations are spray dried on to one or more excipients such as magnesium stearate, mannitol, polyethylene glycol, polymethacrylate, polysorbate, and silicon dioxide. This does not exclude any other dosage or delivery forms Thus there has been shown and described novel Vitamin E formulations, which fulfill all the objects and advantages sought therefor. Many changes, modifications, variations and applications of the subject invention will become apparent to those skilled in the art after consideration of the specification. All such changes, modifications, alterations and other uses and applications which do not depart from the spirit and scope of the invention are deemed to be covered by the invention which is limited only by the claims that follow:

What is claimed is:

1. A soft gelatin capsule comprising a 400 IU once daily dose comprising:
   d-α-tocopherol;
   at least one of an β, γ, or δ tocopherol; and
   at least a second one of an α, β, γ, or δ tocotrienol, further comprising
   alpha carotene, beta carotene, gamma carotene, lycopene, phytosterols and squalene.

2. The soft gelatin capsule of claim 1, wherein said dl-α-tocopherol ester is present in an amount of from 5 mg to 400 mg.

3. The soft gelatin capsule of claim 1, wherein said d-α-tocopherol is present in an amount of from 5 mg to 400 mg.

4. The soft gelatin capsule of claim 1, wherein said at least one α, β, γ, or δ tocopherol is present in an amount of from 5 mg to 200 mg.

5. The soft gelatin capsule of claim 1, wherein said at least one α, β, γ, or δ tocotrienol is present in an amount of from 5 mg to 50 mg, further comprising one or more of:
   α tocotrienol in an amount of from 1 to 30%;
   β tocotrienol in an amount of from 0.1 to 30%;
   γ tocotrienol in an amount of from 1 to 30%; or
   δ tocotrienol in an amount of from 0.1 to 30%.

6. A soft gelatin capsule comprising a 400 IU once daily dose comprising:
   d-α-tocopherol;
   at least one of an β, γ, or δ tocopherol; and
   at least one of an α, β, γ, or δ tocotrienol, further comprising a marker selected the group consisting of coenzyme Q10, rosemary oil, green tea, a lipoic acid, lycopene, grape seed extract, pine bark extract, vitamin C, natural beta carotene, synthetic beta carotene, γ-oryzanol, selenium and lutein.

7. The soft gelatin capsule of claim 6, wherein said dl-α-tocopherol ester is present in an amount of from 5 mg to 400 mg.

8. The soft gelatin capsule of claim 6, wherein said d-α-tocopherol is present in an amount of from 5 mg to 400 mg.

9. The soft gelatin capsule of claim 6, wherein said at least one α, β, γ, or δ tocopherol is present in an amount of from 5 mg to 200 mg.

10. The soft gelatin capsule of claim 6, wherein said at least one α, β, γ, or δ tocotrienol is present in an amount of from 5 mg to 50 mg, further comprising one or more of:
   α tocotrienol in an amount of from 1 to 30%;
   β tocotrienol in an amount of from 0.1 to 30%;
   γ tocotrienol in an amount of from 1 to 30%; or
   δ tocotrienol in an amount of from 0.1 to 30%.

* * * * *